(12) United States Patent
Truschel et al.

(10) Patent No.: US 9,895,081 B2
(45) Date of Patent: Feb. 20, 2018

(54) UPPER AIRWAY RESISTANCE MEASUREMENT DEVICE

(75) Inventors: William A. Truschel, Oakmont, PA (US); Anandi Mahadevan, Monroeville, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 882 days.

(21) Appl. No.: 14/345,426

(22) PCT Filed: Sep. 11, 2012

(86) PCT No.: PCT/IB2012/054709
§ 371 (c)(1),
(2), (4) Date: Mar. 18, 2014

(87) PCT Pub. No.: WO2013/042007
PCT Pub. Date: Mar. 28, 2013

(65) Prior Publication Data
US 2014/0350429 A1   Nov. 27, 2014

Related U.S. Application Data

(60) Provisional application No. 61/537,188, filed on Sep. 21, 2011.

(51) Int. Cl.
*A61B 5/08* (2006.01)
*A61B 5/085* (2006.01)
(Continued)

(52) U.S. Cl.
CPC ......... *A61B 5/085* (2013.01); *A61M 16/0003* (2014.02); *A61M 16/0006* (2014.02);
(Continued)

(58) Field of Classification Search
None
See application file for complete search history.

(56) References Cited

U.S. PATENT DOCUMENTS 3,713,436 A * 1/1973 Hardway, Jr. .......... A61B 5/085
                                                           600/533
4,022,193 A * 5/1977 Franetzki ............... A61B 5/085
                                                           600/533
(Continued)

FOREIGN PATENT DOCUMENTS

CN   102056538 A   5/2011
CN   102905620 A   1/2013
(Continued)

*Primary Examiner* — Navin Natnithithadha
*Assistant Examiner* — Michael R Bloch
(74) *Attorney, Agent, or Firm* — Michael W. Haas

(57) ABSTRACT

A method of estimating the upper airway resistance of a patient using a gas delivery system includes delivering a flow of breathing gas to the patient through the patient circuit of the gas delivery system, superimposing an oscillatory pressure on the flow of breathing gas during an expiratory phase of the patient, determining a first amplitude of an oscillatory component of a gas pressure provided to the patient at an end of the expiratory phase, determining a second amplitude of an oscillatory component of a gas flow provided to the patient at the end of the expiratory phase, determining a first resistance value based on the ratio of the first amplitude to the second amplitude, and determining an upper airway resistance value based on the first resistance value.

18 Claims, 4 Drawing Sheets

(51) Int. Cl.
*A61M 16/00* (2006.01)
*A61M 16/10* (2006.01)

(52) U.S. Cl.
CPC .... *A61M 16/0051* (2013.01); *A61M 16/0066* (2013.01); *A61M 16/0069* (2014.02); *A61M 16/101* (2014.02); *A61M 2016/0027* (2013.01); *A61M 2016/0039* (2013.01); *A61M 2016/0042* (2013.01); *A61M 2230/46* (2013.01)

(56) References Cited

U.S. PATENT DOCUMENTS

| | | | | |
|---|---|---|---|---|
| 4,082,088 | A | * | 4/1978 | Franetzki ............... A61B 5/085 600/533 |
| 4,122,839 | A | * | 10/1978 | Franetzki ............... A61B 5/085 600/533 |
| 4,197,859 | A | * | 4/1980 | Prestele ................. A61B 5/085 600/533 |
| 5,148,802 | A | | 9/1992 | Sanders |
| 5,313,937 | A | | 5/1994 | Zdrojkowski |
| 5,433,193 | A | | 7/1995 | Sanders |
| 5,632,269 | A | | 5/1997 | Zdrojkowski |
| 5,704,345 | A | * | 1/1998 | Berthon-Jones ....... A61B 5/087 128/204.21 |
| 5,803,065 | A | | 9/1998 | Zdrojkowski |
| 5,881,724 | A | * | 3/1999 | Graetz ................... A61B 5/085 128/204.21 |
| 6,029,664 | A | | 2/2000 | Zdrojkowski |
| 6,210,345 | B1 | | 4/2001 | Van Brunt |
| 6,257,234 | B1 | | 7/2001 | Sun |
| 6,539,940 | B2 | | 4/2003 | Zdrojkowski |
| 6,626,175 | B2 | | 9/2003 | Jafari |
| 7,011,091 | B2 | | 3/2006 | Hill |
| 8,485,183 | B2 | * | 7/2013 | Masic ..................... A61B 5/08 128/204.21 |
| 2002/0014240 | A1 | * | 2/2002 | Truschel ............... A61M 16/00 128/204.22 |
| 2003/0062044 | A1 | * | 4/2003 | Berthon-Jones ...... A61M 16/00 128/204.18 |
| 2013/0012828 | A1 | * | 1/2013 | Aylsworth ............. A61B 5/085 600/538 |

FOREIGN PATENT DOCUMENTS

| | | | |
|---|---|---|---|
| CN | 103429290 A | | 12/2013 |
| EP | 2245985 A1 | | 11/2010 |
| WO | WO0228460 A1 | | 4/2002 |
| WO | WO 2005105189 A1 | * | 11/2005 ............ A61B 5/085 |
| WO | WO2009149351 A1 | | 12/2009 |
| WO | WO2010044038 A2 | | 4/2010 |
| WO | WO2010070498 A1 | | 6/2010 |
| WO | WO2011090716 A2 | | 7/2011 |
| WO | WO2011145014 A1 | | 11/2011 |
| WO | WO2012127358 A1 | | 9/2012 |

* cited by examiner

UPPER AIRWAY RESISTANCE MEASUREMENT DEVICE

CROSS-REFERENCE TO RELATED APPLICATIONS

This patent application claims the priority benefit under 35 U.S.C. § 371 of international patent application no. PCT/IB2012/054709, filed Sep. 11, 2012, which claims the priority benefit under 35 U.S.C. § 119(e) of U.S. Provisional Application No. 61/537,188 filed on Sep. 21, 2011, the contents of which are herein incorporated by reference.

BACKGROUND OF THE INVENTION

1. Field of the Invention

The present invention relates to gas delivery systems, such as pressure support systems and other ventilator (invasive or non-invasive) systems, and, more particularly, to a method for estimating the upper airway resistance of a subject using the gas delivery system, and a gas delivery system employing such a method.

2. Description of the Related Art

As is well known in the art, there are numerous situations where it is necessary or desirable to deliver a flow of breathing gas non-invasively to the airway of a patient, i.e., without intubating the patient or surgically inserting a tracheal tube in his or her esophagus. Such therapies are commonly referred to as non-invasive ventilation (NIV) therapies. For example, it is known to non-invasively deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure. NIV therapies involve the placement of a patient interface device including a mask component on the face of a patient, wherein the patient interface device interfaces the ventilator or pressure support device with the airway of the patient. As is also well known in the art, there are also a number of situations where it is necessary or desirable deliver a flow of breathing gas to the airway of a patient invasively, i.e., wherein the patient is intubated or has a surgically inserted tracheal tube.

In providing ventilatory assistance to patients, such as in the various ventilation therapies described above, it is often helpful and/or necessary to be able to obtain an estimate of the upper airway resistance of the patient. However, estimating upper airway resistance in mechanically ventilated patients who have spontaneous respiratory efforts is rather complex, primarily due to that fact that knowledge of the force applied to the respiratory system is required and the fact that, in ventilated patients who have spontaneous respiratory efforts, that force includes a component related to pressure generated by respiratory muscles ($P_{mus}$), which continuously changes during the inflation phase of ventilation.

While there are a number of known methods for patient airway resistance measurement/estimation, including the well known interrupter and forced oscillation techniques, such methods have their drawbacks and limitations. In particular, such known methods can be adversely affected by non-ideal instrumentation and/or leaks in the patient circuit. There is thus room for improvement in the area of patient airway resistance measurement/estimation and a need for a system and method for effectively estimating airway resistance that is not adversely affected by non-ideal instrumentation and/or flow leaks.

SUMMARY OF THE INVENTION

Accordingly, it is an object of the present invention to provide a method of estimating the upper airway resistance of a patient using a gas delivery system that overcomes the shortcomings of conventional estimation methods, such as those shortcomings presented by non-ideal instrumentation and/or flow leaks.

In one embodiment, the method includes delivering a flow of breathing gas to the patient through the patient circuit of the gas delivery system, superimposing an oscillatory pressure on the flow of breathing gas during an expiratory phase of the patient, determining a first amplitude of an oscillatory component of a gas pressure provided to the patient at the end of the expiratory phase, determining a second amplitude of an oscillatory component of a gas flow provided to the patient at the end of the expiratory phase, determining a first resistance value based on the ratio of the first amplitude to the second amplitude, and determining an upper airway resistance value based on the first resistance value.

In another embodiment, a gas delivery system is provided that includes a pressure or flow generating system adapted to produce a flow of breathing gas, a patient circuit operatively coupled to the pressure or flow generating system and structured to deliver the flow of breathing gas to the patient, and a controller operatively coupled to the pressure or flow generating system, wherein the controller is structured/programmed to estimate the upper airway resistance of a patient by implementing the method just described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
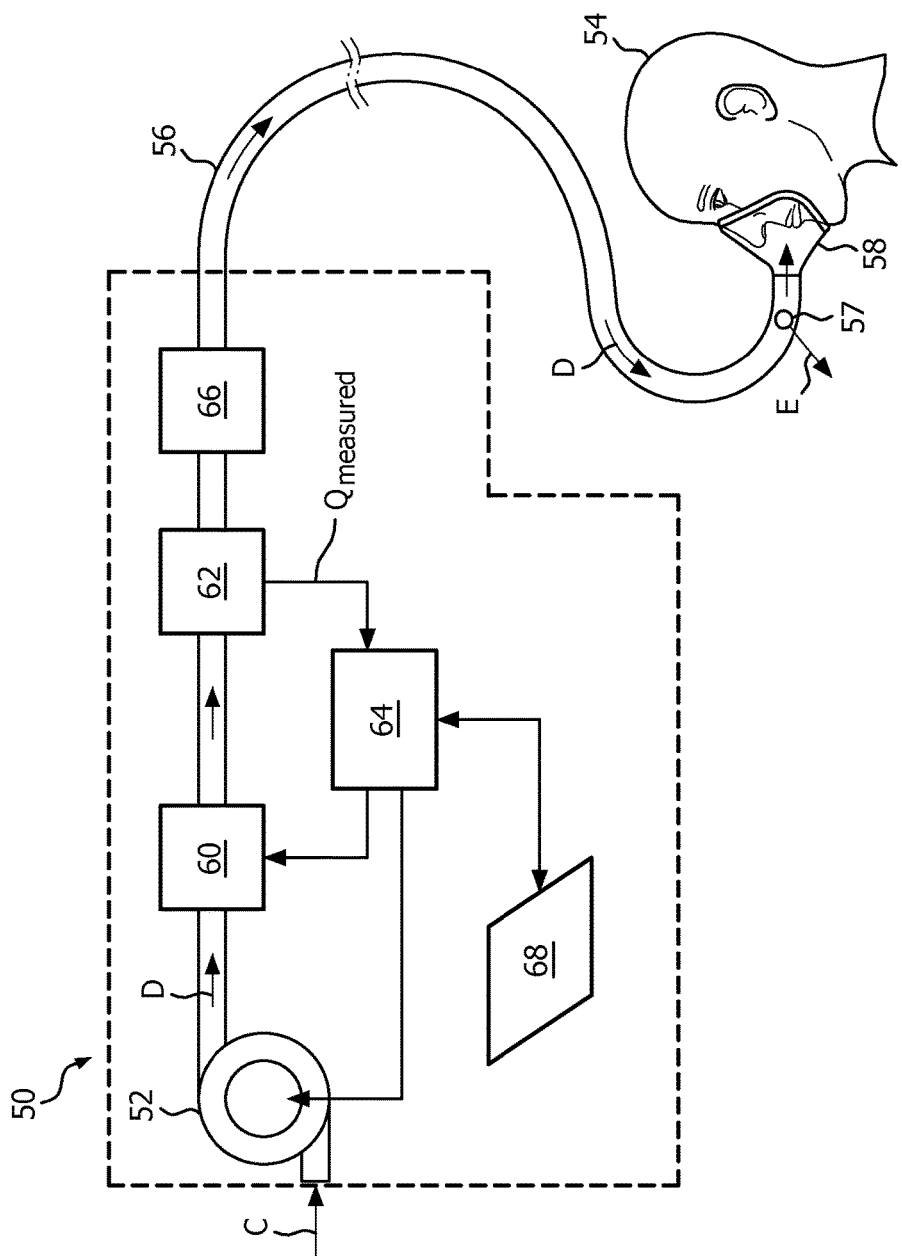
FIG. 1 is a schematic diagram of pressure support system according to one particular, non-limiting embodiment in which the upper airway resistance estimation methodology of the present invention may be implemented.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of a pressure support system 50 according to one particular, non-limiting embodiment in which the upper airway resistance estimation methodology of the present invention may be implemented. It should be understood that pressure support system 50, which is a NIV system, is meant to be exemplary only for purposes of illustrating and describing the present invention, and that the present invention may be implemented and employed in other types of gas delivery systems, such as, without limitation, an invasive ventilator system. One such alternative gas delivery system is described in PCT Publication No. WO 2010/044038, entitled "Volume Control in a Medical Ventilator," assigned to the assignee of the present invention, the disclosure of which is incorporated herein by reference. Thus, the present invention may be employed in any type of gas delivery system where it is necessary or desirable to estimate upper airway resistance of the patient.

Referring to FIG. 1, pressure support system 50 includes a gas flow/pressure generator 52, such as a blower used in a conventional CPAP or bi-level pressure support device, piston, bellows, compressor, or any other device that receives breathing gas, generally indicated by arrow C, from any suitable source, e.g., a pressurized tank of oxygen or air, the ambient atmosphere, or a combination thereof. Gas flow/pressure generator 52 generates a flow of breathing gas, such as air, oxygen, or a mixture thereof, for delivery to an airway of a patient 54 at relatively higher and lower pressures, i.e., generally equal to or above ambient atmospheric pressure.

The pressurized flow of breathing gas, generally indicated by arrow D from gas flow/pressure generator 52, is delivered, via a delivery conduit 56, to breathing mask or patient interface 58 of any known construction, which is typically worn by or otherwise attached to patient 54 to communicate the flow of breathing gas to the airway of the patient. Delivery conduit 56 and patient interface device 58 are typically collectively referred to as a patient circuit.

Although not shown in FIG. 1, the present invention also contemplates providing a secondary flow of gas, either alone or in combination with the primary flow of gas (arrow C) from atmosphere. For example, a flow of oxygen from any suitable source, such as an oxygen concentrator, or oxygen storage device (liquid or gas), can be provided upstream of gas flow/pressure generator 52 or downstream of the gas flow generator, for example, in the patient circuit or at the patient interface device, to control the fraction of inspired oxygen delivered to the patient.

Pressure support system 50 shown in FIG. 1 is a single-limb system, meaning that the patient circuit includes only delivery conduit 56 connecting the patient to the pressure support device. An exhaust vent 57 is provided in the delivery conduit 56 for venting exhaled gasses (e.g., $CO_2$) from the system to atmosphere as indicated by arrow E. In the exemplary embodiment, the patient circuit is a passive circuit and exhaust vent 57 is a fixed orifice. It should be noted that exhaust vent 57 can be provided at other locations in addition to or instead of in delivery conduit 56, such as in the patient interface device 58. It should also be understood that exhaust vent 57 can have a wide variety of configurations depending on the desired manner in which gas is to be vented from the pressure support system.

In the illustrated exemplary embodiment of the present invention, patient interface 58 is a nasal/oral mask. It is to be understood, however, that patient interface 58 can include a nasal mask, nasal pillows, tracheal tube, endotracheal tube, or any other device that provides the gas flow communicating function. Also, for purposes of the present invention, the phrase "patient interface" can include delivery conduit 56 and any other structures that connect the source of pressurized breathing gas to the patient.

It is to be understood that various components may be provided in or coupled to the patient circuit. For example, a bacteria filter, pressure control valve, flow control valve, sensor, meter, pressure filter, humidifier and/or heater can be provided in or attached to the patient circuit. Likewise, other components, such as muffler and filters can be provided at the inlet of gas flow/pressure generator 52 and at the outlet of valve 60 (described below).

In the illustrated embodiment, pressure support system 50 includes a pressure controller or flow controller in the form of a valve 60 provided in delivery conduit 56. Valve 60 controls the pressure or the flow of breathing gas from gas flow/pressure generator 52 delivered to patient 54. For present purposes, gas flow/pressure generator 52 and valve 60 are collectively referred to as a "pressure generating system" because they act in concert to control the pressure and/or flow of gas delivered to the patient.

It should be apparent that other techniques for controlling the pressure or the flow delivered to the patient by the gas flow/pressure generator, such as varying the blower speed, either alone or in combination with a pressure control valve, are contemplated by the present invention. Thus, valve 60 is optional depending on the technique used to control the pressure of the flow of breathing gas delivered to the patient. If valve 60 is eliminated, the pressure generating system corresponds to gas flow/pressure generator 52 alone, and the pressure of gas in the patient circuit is controlled, for example, by controlling the motor speed of the gas flow/pressure generator.

Pressure support system 50 further includes a flow sensor 62 that measures the flow of the breathing gas within delivery conduit 56. In the particular embodiment shown in FIG. 1, flow sensor 62 is interposed in line with delivery conduit 56, most preferably downstream of valve 60. Flow sensor 62 generates a flow signal, $Q_{measured}$, that is provided to controller 64 and is used by controller 64 to determine the flow of gas at patient 54 ($Q_{patient}$).

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 1, and unknown leaks from the system, such a leaks at the mask/patient interface. The present invention contemplates using any known or hereafter developed technique for calculating leak flow $Q_{leak}$, and using this determination in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Pressure support system 50 also includes a pressure sensor 66 that measures the pressure of the breathing gas within delivery conduit 56. In the particular embodiment shown in FIG. 1, pressure sensor 66 is interposed in line with delivery conduit 56.

Of course, other techniques for measuring the respiratory flow of patient 54 and the pressure of gas delivered to patient 54 are contemplated by the present invention, such as, without limitation, measuring the flow and/or pressure directly at patient 54 or at other locations along delivery conduit 56, measuring patient flow and/or pressure based on the operation of flow generator 52, and measuring patient flow and/or pressure using a sensor upstream of valve 60.

Controller 64 includes a processing portion which may be, for example, a microprocessor, a microcontroller or some other suitable processing device, and a memory portion that may internal to the processing portion or operatively coupled to the processing portion and that provides a storage medium for data and software executable by the processing portion for controlling the operation of pressure support system 50, including estimating upper respiratory resistance as described in greater detail herein.

Input/output device 68 is provided for setting various parameters used by the variable positive airway pressure support system, as well as for displaying and outputting information and data to a user, such as a clinician or caregiver. It is to be understood that the present invention contemplates providing input/output terminals so that the operation information and data collected by the pressure support system can be monitored and controlled remotely.

In one exemplary embodiment, the present invention provides an improved methodology for estimating the upper airway resistance of a patient connected to a mechanical ventilator with a passive circuit, such as pressure support system 50, that is based on infrasonic wave excitation (i.e., frequencies below 20 Hz). For illustrative purposes, that improved methodology will be described as being implemented in pressure support system 50. It will be understood, however, that that is meant to be exemplary only and that the improved methodology may be implemented in other suitable gas delivery systems.

The method of infrasonic wave excitation of the present invention is founded on the principle that the upper airway of a subject will exhibit various magnitudes of oscillating flow (i.e., rate of gas flow) when excited with a fixed magnitude of oscillatory pressure based on the degree of upper airway obstruction. As noted elsewhere herein, the passive circuit of pressure support system 50 contains a fixed orifice (exhaust vent 57) of various size leak for $CO_2$ removal. As also noted herein, patient interface 58 will likely also contain a variable leak at the patient mask. The variation in leak produces a variation in the flow response to an oscillatory pressure. This response of the leak, if not accounted for, affects the calculation of the upper airway resistance.

The upper airway resistance estimation method of the present invention anticipates that the patient airway and lungs will have a predicted flow response when excited with an oscillatory pressure wave that is primarily based upon the upper airway resistance. This method not only contains a robust method for approximating the flow response based on inputs from sensors located within pressure support system 50, but provides a method based on the estimates of the upper airway resistance in the presence of variable leak. The estimates of upper airway resistance provide a quantitative degree of patient obstructions inherent in sleep breathing disorders such as obstructive sleep apnea. This resistance measurement is useful for either the diagnosis or treatment of upper airway collapse. With regard to treatment, this estimation can be used within an automatic EPAP or CPAP machine, such as pressure support system 50, to prescribe adjustable pressure as the airway patency changes during sleep.

Before describing the method of the present invention in detail, a brief description of selected relevant respiratory mechanics principles will be provided. An electrical analog for the lung mechanics of a human subject is a simple RC series circuit. It is appreciated that in human respiration, the resistance term is often non-linear and flow dependant and very dissimilar to a linear electrical resistor in many ways. A linear approximation to the upper airway resistance is only reasonable under the conditions of quasi-static pressure and flow conditions. The upper airway is often described as a flexible tube due to the fact that the walls of the upper airway consist of soft tissue including the uvula and pharyngeal muscles that surrounds the airway. The Starling resistor has been an effective experimental model for simulation and testing of the upper airway mechanics.

CPAP has been shown as an effective tool in stinting the upper airway in an open or low resistance state. The positive pressure of CPAP will both prevent and treat the collapse of the upper airway. The lower bronchials offer some further airway resistance and introduce a small inertance term ignored in the RC model. The inertance becomes important during periods of either high inspiratory or expiratory flow, and because, as will be described elsewhere herein, the method of the present invention is only concerned with making measurements when patient flow is zero or close to zero (at the end of the expiratory phase), the inertance may be ignored in the method of the present invention.

Furthermore, the electrical capacitance term in the RC model is associated with the elastance of the lung itself. It has been experimentally shown that this elastance term is nearly constant over the range of normal breathing patterns and is approximately 50 ml/cmH$_2$O in healthy individuals. Finally, there are external forces applied over the outer surface of the lungs by the contraction of the diaphragm at the onset of inspiration. This contraction produces a negative internal pressure in the lung cavity that induces flow from the upper airway to the lung.

Expiration during sleep is generally passive. Expiratory flow is accomplished when the elastic recoil of the lungs increases the pressure of gas within the lungs (due to the reduction in volume) and produces the flow of $CO_2$ enriched gas out of the body. Again, considering the flow at the very end of expiration, during the expiratory pause or quiet phase of breathing, allows the method of the present invention to ignore the pressures induced by the external forces of the patient muscles.

Therefore, the respiratory model for purposes of the method of the present invention is well described as the following first order differential Equation (1):

$$P_{app} + P_{mus} = R \cdot Q_p + E \cdot V$$

where $P_{app}$ is the applied pressure by the mechanical ventilator or CPAP device (pressure support system 50 in the exemplary embodiment), $P_{mus}$ the applied pressure by the diaphragmatic muscles, R is a linear approximation of the lumped resistance of the respiratory system, $Q_p$ is the patient flow, E is the elastance of the lung and V is the volume in the lung. Furthermore, V is set forth in the following Equation (2):

$$V = \int Q_p dt$$

According to an aspect of the present invention, an oscillatory pressure is superimposed on the pressure therapy being delivered to the patient (by pressure support system 50 in the exemplary embodiment) during the expiratory phase. In one exemplary, non-limiting embodiment, the oscillatory pressure has a magnitude of 1 to 2 cmH$_2$O and a frequency below 20 Hz. The respiratory components in Equation (1) can be estimated by taking the ratio of applied pressure to applied flow and expressing this ratio in complex form. Ignoring the muscle pressure, we begin with the applied pressure during the expiratory phase including the oscillations as set forth in the following Equation (3):

$$P_{app}(t) = PEEP + P_{amp} \sin \omega t$$

where $P_{amp}$ is the amplitude of the pressure oscillations and $\omega$ is the angular frequency of the oscillations. This pressure, $P_{amp}$, can be measured or estimated and filtered to remove the PEEP (constant) term, with the result being the following Equation (4):

$$P_{app\_filtered}(t) = P_{amp} \sin \omega t$$

At the end of expiration (i.e., when patient flow has returned to zero), $P_{mus}$ is zero and the non-linear effects of patient flow on the upper airway resistance have vanished because the patient flow is also near zero. The anticipated flow response to an oscillatory pressure applied during the expiratory pause is given simply by the lung components, approximated in Equation (5) below (as a linear representation as in Equation (1)):

$$Q_p(t) = P_{amp} \sin \omega t \cdot \frac{1}{R + 1/sC},$$

where $s = \sqrt{-1} \cdot \omega$ or $s = j\omega$. Taking the ratio of the applied pressure and flow gives the following Equation (6):

$$\frac{P_{app\_filtered}}{Q_p} = R - j\frac{1}{C}.$$

Figure 2:
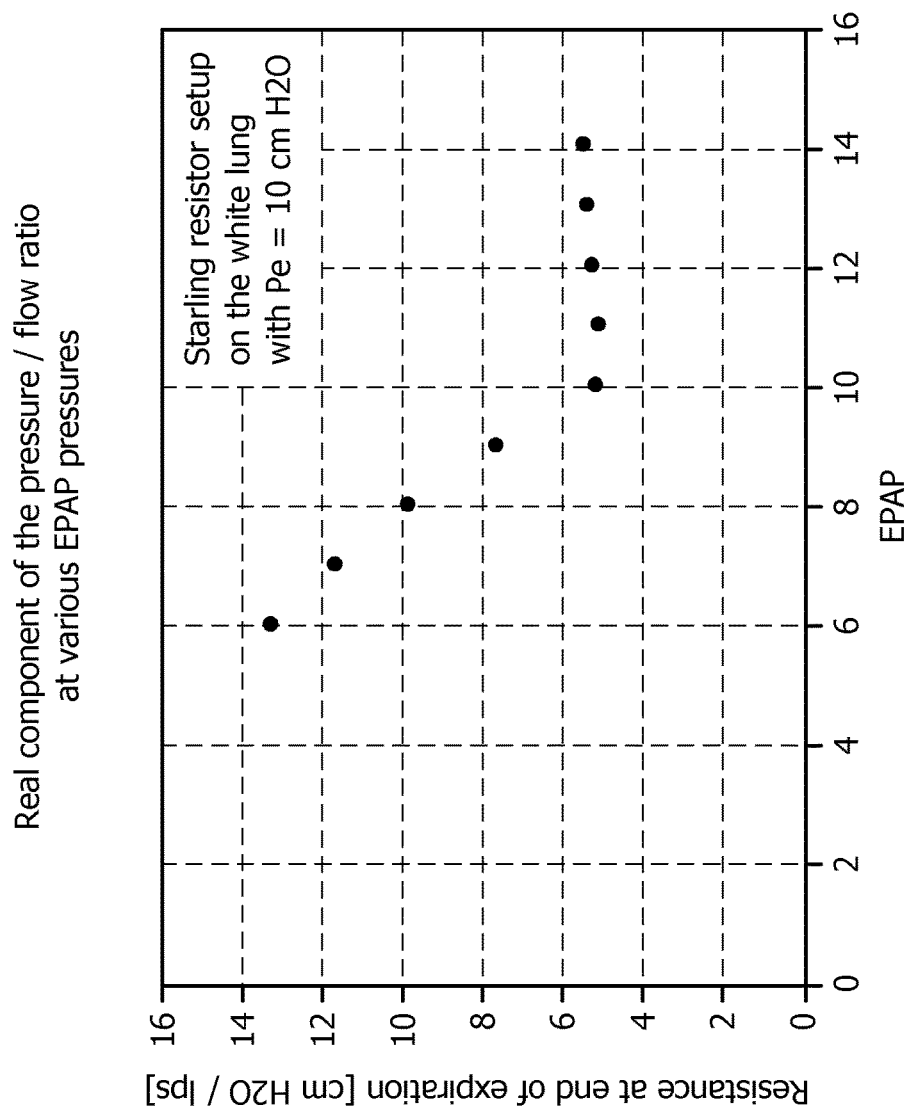
FIG. 2 is a graph showing the results of computing the ratio of applied oscillatory pressure to flow at the end of the expiratory phase on a test lung.

There are various mathematical techniques to collect a series of data points and express them in complex form. Equation (6) shows that if the real part of the ratio is estimated, a good indication of the airway resistance is provided. The complex part is the negative inverse of the lung compliance. If an algorithm were solely interested in the airway resistance, then the real part of the applied pressure and flow ratio at the end of expiration is a good estimate of airway resistance. Using this technique solely with Starling resistor simulations of collapsed airways has been successful in extracting airway resistance with laboratory grade instrumentation. FIG. 2 shows the results of this measurement technique.

In particular, FIG. 2 shows the results of computing the ratio of applied oscillatory pressure to flow at the end of the expiratory phase on a test lung. The ratio was modeled using the linear least squared method fitting the instrument data in the form of Z=A cos $\omega$t+B sin $\omega$t. The real part of the estimate clearly showed that as the flexible tube was expanded by the increasing EPAP pressure, the resistance decreased until the critical pressure (10 cm H20) above which it remained relatively constant. This was the expected result of the Starling resistor model. This test was done in the presence of a constant leak orifice and this orifice was unaccounted for.

It has been discovered that a number of complications arise in connection with the above described embodiment when non-ideal instrumentation is used. First, consider that a pressure and flow transducer (e.g., flow sensor 62 and pressure sensor 66 of pressure support system 50) have a non-zero response time. Therefore, the measurement of time varying signals by a non-ideal transducer will induce a make-believe imaginary component as one or both of the signals have a phase delay from the actual signal.

Further complications arise when pressure is measured away from the actual mechanical components. This distance between the measurement and the physical model results in a transmission delay in the pressure that is not indicated by the sensing system. The incompressible nature of the fluid in the system does not produce the equivalent transmission delay in the flow signal. These non-equivalent delays produce a further make-believe phase shift in the results and decrease the accuracy of the measurement.

Perhaps the most difficult complication of the above embodiment of the method arises when accuracy is needed to correct the lung mechanics model when variable leak is present. Not only does the leak influence the measurement, it also muddies the phase shift in the flow signal due to the fact that the leaky component is often physically removed from the sensors.

These complications have driven the present inventors to consider an alternative method for the estimation upper of airway resistance measurement based on the flow response. That alternative method is described below.

Returning to Equation (5), the R term is redefined as the parallel combination of the respiratory resistance and the leak orifice resistance as set forth in the following Equation (7):

$$R_{equiv} = \frac{R_{leak} \cdot (R + 1/sC)}{R + R_{leak} + 1/sC}, www$$

where $R_{equiv}$ is the equivalent total resistance of the airway in parallel with the leak resistance, and $R_{leak}$ is a linear approximation of $$\frac{dP}{dQ}$$

of the leak flow out of the leak orifice at a given pressure (namely EPAP). An exemplary algorithm for computing $R_{leak}$ is described elsewhere herein. The flow response is given by the following Equation (8):

$$Q(s) = \frac{P_{app}(s)}{R_{equiv}(s)}.$$

Substituting Equation (4) into Equation (1) and solving Equation (1) with $P_{mus}=0$ (designating the lung time constant, $\tau=R \cdot C$), the solution to Equation (1) in the time domain during the expiratory phase is given by the following Equation (9):

$$Q(t) = P_{amp\_filtered}\sqrt{A^2 + \left(\frac{B}{\omega}\right)^2}\sin\left(\omega t + \left(\tan^{-1}\left(\frac{B}{\omega A}\right) - \frac{\pi}{2}\right)\right) + De^{-t/\tau}$$

where $$A = \frac{\omega C}{1+\omega^2\tau^2}, B = \frac{\omega C}{\tau} + \frac{\omega}{R_{leak}} + \frac{\omega C}{\tau(1+\omega^2\tau^2)},$$

and $$D = \frac{-\omega\tau C}{1+\omega^2\tau^2}.$$

In steady state after the final exponential term has vanished, the amplitude of the flow waveform is given by the following Equation (10):

$$Q_{amp} = P_{amp\_filtered}\sqrt{A^2 + \left(\frac{B}{\omega}\right)^2}.$$

And subsequently assuming that the phase angle between pressure flow is small, Equation (8) provided the following Equation (11):

$$R_{equiv} \cong \left(\sqrt{A^2 + \left(\frac{B}{\omega}\right)^2}\right)^{-1},$$

assuming the following Equation (12) to be true:
ass $$\tan^{-1}\left(\frac{B}{\omega A}\right) \cong \frac{\pi}{2}.$$

The assumption of Equation (12) can be verified by inspection for reasonable values in one exemplary, non-limiting embodiment, as set forth in the following Tables 1-6.

TABLE 1

Healthy Lung - Normal Leak

| | | |
|---|---|---|
| Rleak | 25 | cm H20/lps |
| C | 0.05 | liters/cm H20 |
| R | 5 | cm H20/lps |
| w | 31.4 | rad/sec |
| A | 2.62085E−08 | lps |
| B | 7.636283444 | |
| tan−1(B/Aw) | 1.571 | rad |
| phase shift | 0.000 | rad |

TABLE 2

Healthy Lung - High Leak

| | | |
|---|---|---|
| Rleak | 13 | cm H20/lps |
| C | 0.05 | liters/cm H20 |

TABLE 2-continued

Healthy Lung - High Leak

| | | |
|---|---|---|
| R | 5 | cm H20/lps |
| w | 31.4 | rad/sec |
| A | 2.62085E−08 | lps |
| B | 8.79566806 | |
| tan−1(B/Aw) | 1.571 | rad |
| phase shift | 0.000 | rad |

TABLE 3

Restrictive Lung - Low Leak

| | | |
|---|---|---|
| Rleak | 25 | cm H20/lps |
| C | 0.02 | liters/cm H20 |
| R | 5 | cm H20/lps |
| w | 31.4 | rad/sec |
| A | 6.55212E−08 | lps |
| B | 8.114290176 | |
| tan−1(B/Aw) | 1.571 | rad |
| phase shift | 0.000 | rad |

TABLE 4

Restrictive Lung - High Leak

| | | |
|---|---|---|
| Rleak | 13 | cm H20/lps |
| C | 0.02 | liters/cm H20 |
| R | 5 | cm H20/lps |
| w | 31.4 | rad/sec |
| A | 6.55212E−08 | lps |
| B | 9.273674792 | |
| tan−1(B/Aw) | 1.571 | rad |
| phase shift | 0.000 | rad |

TABLE 5

Obstructive Patient - High Leak

| | | |
|---|---|---|
| Rleak | 13 | cm H20/lps |
| C | 0.02 | liters/cm H20 |
| R | 20 | cm H20/lps |
| w | 31.4 | rad/sec |
| A | 4.09507E−09 | lps |
| B | 3.995274155 | |
| tan−1(B/Aw) | 1.571 | rad |
| phase shift | 0.000 | rad |

TABLE 6

Obstructive Patient - Low Leak

| | | |
|---|---|---|
| Rleak | 25 | cm H20/lps |
| C | 0.02 | liters/cm H20 |
| R | 20 | cm H20/lps |
| w | 31.4 | rad/sec |
| A | 4.09507E−09 | lps |
| B | 2.83588954 | |
| tan−1(B/Aw) | 1.571 | rad |
| phase shift | 0.000 | rad |

Results show that at 5 Hz, no reasonable combination of these parameters produces any significant phase shift. Expanding Equation (11) and assuming that the product of the frequency and lung time constant is much greater than 1 means that Equation (11) can be approximated as the following Equation (13):

$$R_{equiv} \cong \left( \sqrt{\left(\frac{1}{\omega CR_{lung}^2}\right)^2 + \left(\frac{1}{R_{lung}} + \frac{1}{R_{leak}} + \frac{1}{\omega^2 C^2 R_{lung}^3}\right)^2} \right)^{-1}.$$

Then, further assuming that the first squared term and the third term inside the second parentheses are near zero leaves the following Equation (14):

$$R_{equiv} \cong \left(\frac{1}{R_{lung}} + \frac{1}{R_{leak}}\right)^{-1},$$

thereby showing that the ratio of amplitudes is approximately equal to the parallel combination of the leak resistance ($R_{leak}$) and the airway resistance ($R_{lung}$). These approximations using the scenarios above (Tables 1-6) show that Equation (14) approximates Equation (11) reasonably at 5 Hz, with small errors occurring when the lung has a low time constant (<0.2 seconds). These results are shown in Table 7 below.

TABLE 7

| | Eq. (11) (cm H$_2$O/lps) | Eq. (14) (cm H$_2$O/lps) | $R_{lung}$ est. (cm H$_2$O/lps) | Error (cm H$_2$O/lps) |
|---|---|---|---|---|
| Healthy Lung - Normal Leak | 4.11 cm H$_2$O/lps | 4.17 | 4.92 | 0.08 |
| Healthy Lung - High Leak | 3.57 | 3.61 | 4.92 | 0.08 |
| Rest. Lung - Low Leak | 3.87 | 4.17 | 4.58 | 0.42 |
| Rest. Lung - High Leak | 3.39 | 3.61 | 4.58 | 0.42 |
| Obst. Patient - High Leak | 7.86 | 7.88 | 19.87 | 0.13 |
| Obst. Patient - Low Leak | 11.07 | 11.11 | 19.87 | 0.13 |

The results show that if the airway resistance is low (<5 cmH20/lps) and the patient becomes obstructive (C<0.02 l/cmH20), the equivalent resistance may be underestimated when the compliance effect is neglected. These errors can be accounted for in various simple ways, including: (i) providing compliance compensation and use Equation (11); (ii) increasing the frequency of the oscillations above 14 Hz to reduce the percent error in all scenarios to less than 1%, and (iii) providing robustness in the handling of estimated lung resistance when it is low. The neglect of compliance always causes an underestimation of the lung resistance.

For clarity, a point that was established above that may seem like a contradiction will now be reiterated. The exercise above shows that there is no anticipated phase shift between the actual patient pressure and the total flow including the leak. When using the method described in Equation (6), any measured phase shift is an artifact of imperfect sensors and these errors result in inaccuracies in resistance estimation. The new method described by Equation (14) is not subject to these types of errors. In the robust approximation method, any phase shift created by sensing delays or pressure wave propagation delays will not affect the resistance measurement based solely on amplitude.

As is described herein, the airway resistance estimation method of the present embodiment requires the oscillatory amplitude components of the pressure and flow signals. As will be appreciated, a high pass filter is all that is theoretically required to extract the oscillatory amplitude of the pressure and flow signals. However, in the exemplary embodiment, it is practical to replace a high pass filter with a bandpass filter to remove any high frequency noise. In the exemplary embodiment, the bandpass filter is a 8th order Butterworth digital filter centered at 5 Hz with a passband 2 Hz wide. This filter is described by the transfer function.

$$H(z) = \frac{b_0 + b_1 z^{-1} + b_2 z^{-2} + b_3 z^{-3} + b_4 z^{-4} + b_5 z^{-5} + b_6 z^{-6} + b_7 z^{-7} + b_8 z^{-8}}{1 + a_1 z^{-1} + a_2 z^{-2} + a_3 z^{-3} + a_4 z^{-4} + a_5 z^{-5} + a_6 z^{-6} + a_7 z^{-7} + a_8 z^{-8}}$$

A={1.0000 −7.3107 23.7252 −44.6168 53.1630 −41.0966 20.1293 −5.7134 0.7199}

B={0.00001329 0 −0.00005317 0 0.00007976 0 −0.00005317 0 0.00001329}

Figure 3:
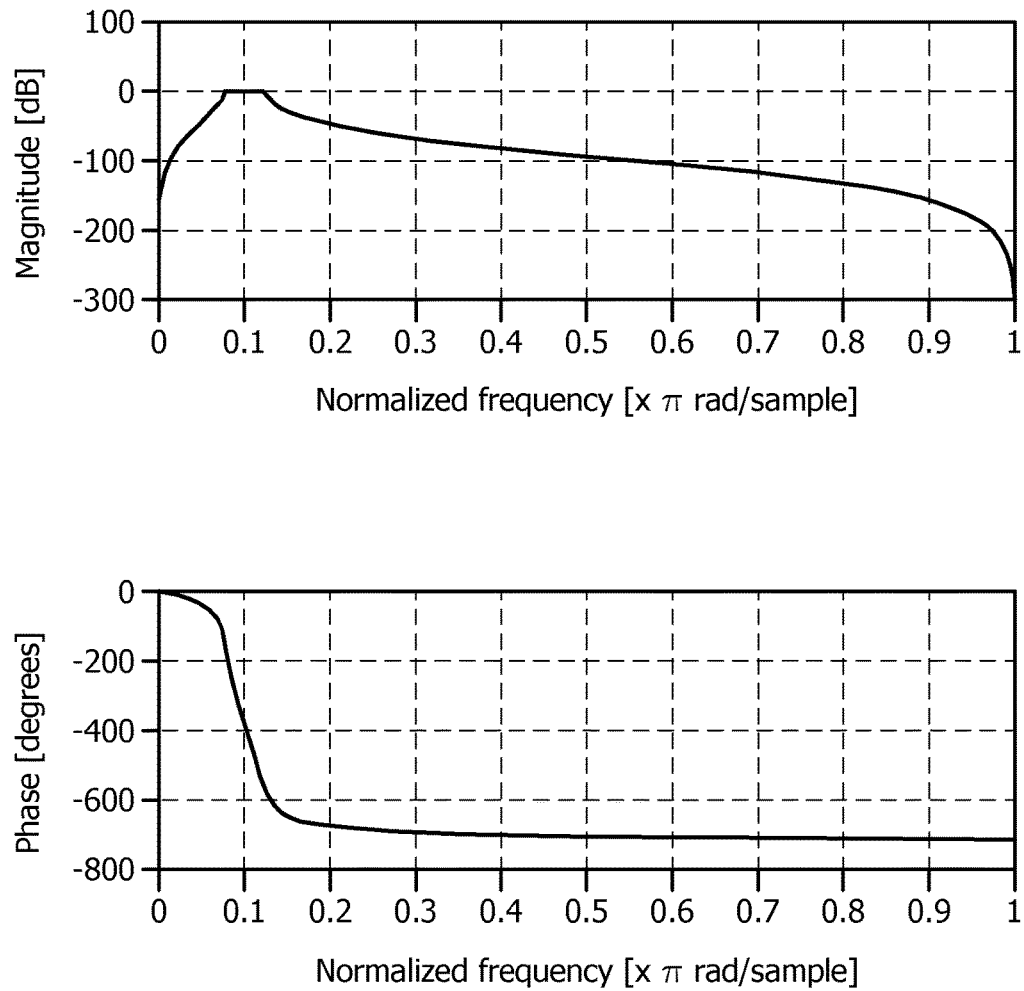
FIG. 3 provides two plots showing the frequency response of an exemplary band pass filter that may be employed in implementing the present invention.

The frequency response of this exemplary filter is shown in FIG. 3. The frequency is appropriate when the Fs=100 Hz and the desired frequency is 5 Hz (0.1× Nyquist frequency). The filter coefficients are scaled by 2^24 for integer arithmetic.

In the current embodiment, the measurement of the equivalent resistance, $R_{equiv}$, is accomplished by taking the ratio of the amplitude of the oscillatory component of the patient pressure measurement or estimation to the amplitude of the oscillatory component of the patient flow at the end of the expiratory phase. The measurement of a signal amplitude can be done via numerous methods. The exemplary method is by means of the root mean square (rms) calculation. Considering again that the signals may have imaginary phase offsets from each other, it is important that only 1 cycle ($2\pi$) of points are used in the calculation (e.g. 20 samples for a 5 Hz signal sampled at 10 msec). Equations (15a), (15b) and (16), respectively, below show such an rms calculation of the amplitude of the oscillatory component of the patient pressure ($P_{amp}$), the oscillatory component of the patient flow ($Q_{amp}$), and the equivalent resistance ($R_{equiv}$):

$$P_{amp} = \sqrt{2}\sqrt{\frac{\sum_{n=1}^{20} P_{P_{meas}}^2}{20}},$$

$$Q_{amp} = \sqrt{2}\sqrt{\frac{\sum_{n=1}^{20} Q_{meas}^2}{20}},$$

$$R_{equiv} = \sqrt{\frac{\sum_{n=1}^{20} P_{Pmeas}^2}{\sum_{n=1}^{20} Q_{meas}^2}}.$$

In the current embodiment, the measurements from Equation (16) (i.e., the determined $R_{equiv}$) are used with Equation (14) and an $R_{leak}$ value (described elsewhere herein) to extract the upper airway resistance ($R_{lung}$).

As noted elsewhere herein, the amplitude of the pressure provided to the patient 54 may be measured at a number of different locations. For example, pressure may be directly sensed/measured at patient 54 (proximal pressure sensing) and used in the calculations described herein. However, when proximal pressure sensing is unavailable, the amplitude of the patient pressure must be derived from the measurement of the outlet pressure amplitude as measured by, for example, pressure sensor 66. There are two significant loss terms in a patient circuit. The first is a restrictive drop derived from Pouiselle's law for flow in tubes and pipes. The second loss is due to the inertance of the tube. The restrictive drop has been empirically determined to be approximately 0.27 cm H₂O/liter per second. The inertance is given by the formula of Equation (17) below:

$$I = \frac{\rho \cdot l}{A},$$

where $\rho$ is the density of the air flowing through the tube, l is the length of the tube and A is the cross sectional area of the tube. Assuming the air density is 1.2 kg/m^3, the inertance (I) of a 6', 22 mm tube is given by the following Equation (18):

$$I = .062 \frac{cm\ H20 \cdot s^2}{L}.$$

The outlet pressure is measured and the outlet flow is measured. To compensate for the drop in the circuit, the pressure drop from Poiseusille's law and the pressure drop from the inertance are subtracted from the outlet pressure in real time to estimate the patient pressure as shown in the following Equation (19):

$$P_{Pamp} = P_{amp} - R_{circuit} \cdot Q_{filtered} + I \frac{dQ_{filtered}}{dt},$$

where $R_{circuit}$ is the linear approximation of dP/dQ through the circuit due to Poiseusille's Law and $Q_{filtered}$ is the 5 Hz component of the flow signal.

As described above, the present exemplary embodiment employs a resistance parameter associated with a variable leak ($R_{leak}$), which is a representation of the linear pressure drop as a function of changing leak flow. Considering that there will be surely a transmission delay from the machine outlet to the patient end of the tube, it is important that leak estimation doesn't use the 5 Hz amplitude and uses a slower process. That process, regardless of method, represents leak flow as a function of pressure. To convert this function to a meaningful value for the leak resistance, in the exemplary embodiment, the formula provided in Equation (20) below is used to determine $R_{leak}$:

$$R_{leak} = \frac{60 \cdot 1\ cm\ H20}{Q_{leak}(PEEP+0.5\ cm\ H20) - Q_{leak}(PEEP-0.5\ cm\ H20)},$$

where the 60 will convert liters per minute to liters per second, but $R_{leak}$ should be expressed in units of cmH₂O/(liters per sec).

Finally, as stated elsewhere herein, the goal of the methodology of the present invention is to estimate the upper airway resistance for the diagnosis and treatment of airway collapse. After the amplitude of the patient pressure has been estimated and considering the flow through outlet is the combined flow of leak and patient flow, the upper airway resistance ($R_{lung}$—lung resistance) is estimated by equating equation (14) to the measurement found from equation (16). The result is the following Equation (21):

$$R_{lung} = \frac{R_{equiv} \cdot R_{leak}}{R_{leak} - R_{equiv}}.$$

Figure 4:
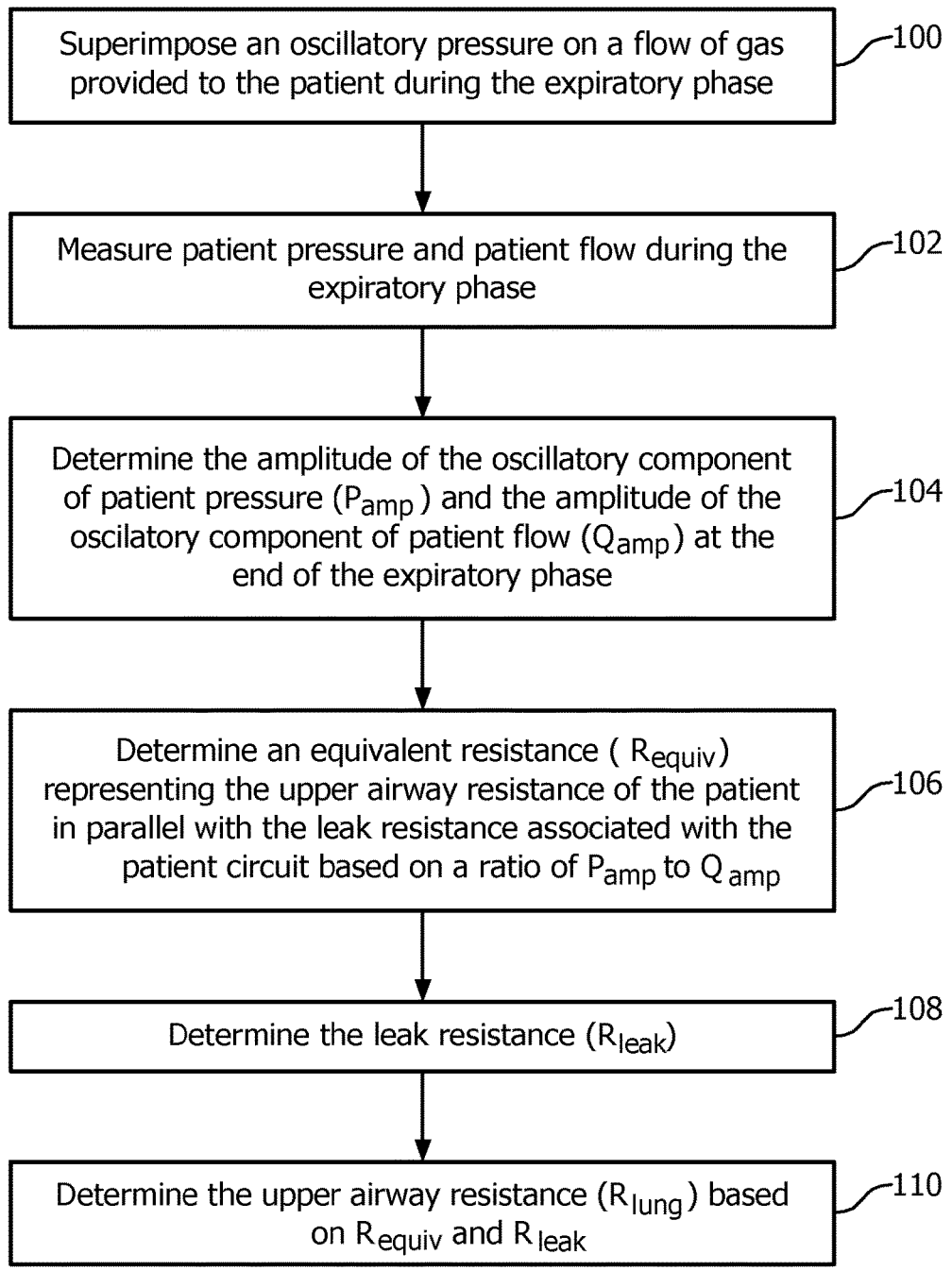
FIG. 4 is a flowchart that illustrates an exemplary embodiment of the method of upper airway resistance estimation of the present invention as implemented in the pressure support system of FIG. 1.

Referring now to FIG. 4, a flowchart is provided that illustrates an exemplary embodiment of the method of upper airway resistance estimation of the present invention described in detail herein as implemented in pressure support system 50, and in particular as implemented in one or more routines programmed in controller 64. The method begins at step 100, wherein controller 64 causes the pressure generating system of pressure support system 50 to superimpose an oscillatory pressure (e.g., an infrasonic wave) onto the flow of breathing gas that is being delivered to patient 54 through the patient circuit during the expiratory phase. Next, at step 102, patient pressure and patient flow (rate of gas flow) are measured during the expiratory phase by pressure sensor 66 and flow sensor 62, respectively. That data is provided to controller 64. Then, at step 104, controller 64 determines: (i) the amplitude ($P_{amp}$) of the oscillatory component (i.e., the component resulting from the superimposed oscillatory pressure) of the pressure provided to patient 54 at the end of the expiratory phase as described elsewhere herein and (ii) the amplitude ($Q_{amp}$) of the oscillatory component (i.e., the component resulting from the superimposed oscillatory pressure) of the flow provided to patient 54 at the end of the expiratory phase as described elsewhere herein.

In the exemplary embodiment, both $P_{amp}$ and $Q_{amp}$ are determined using an rms calculation as described in detail elsewhere herein (see Equations 15a and 15b). Next, at step 106, controller 64 determines an equivalent resistance value ($R_{equiv}$) that represents the parallel combination of the upper airway (respiratory) resistance and the leak orifice resistance, wherein leak orifice resistance is the linear approximation of $$\frac{dP}{dQ}$$

of the leak flow out of the leak orifice of the patient circuit of pressure support system 50 at a given pressure. The equivalent resistance value ($R_{equiv}$) is determined based on a ratio of $P_{amp}$ to $Q_{amp}$ (in the exemplary embodiment, $R_{equiv}=P_{amp}/Q_{amp}$.). Next, at step 108, the current leak orifice resistance ($R_{leak}$) at the end of the expiratory phase is determined using a suitable technique, such as that described herein in connection with Equation (20). Finally, at step 110, the upper airway resistance ($R_{lung}$) is determined (estimated) based on $R_{equiv}$ and $R_{leak}$. In the exemplary embodiment, step 110 is performed using Equation (21).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of treating a patient using a gas delivery system, comprising:
    generating a flow of breathing gas using a pressure or flow generator of the gas delivery system;
    delivering the flow of breathing gas to the patient through a patient circuit of the gas delivery system;
    superimposing an oscillatory pressure on the flow of breathing gas delivered through the patient circuit using the pressure or flow generator during an expiratory phase of the patient;
    generating a patient pressure signal using a pressure sensor of the gas delivery system during the expiratory phase, the patient pressure signal being indicative of a pressure provided to the patient through the patient circuit;
    generating a patient flow signal using a flow sensor of the gas delivery system during the expiratory phase, the patient flow signal being indicative of a rate of gas flow provided to the patient through the patient circuit;
    determining a first amplitude of an oscillatory component of a gas pressure provided to the patient at an end of the expiratory phase based on the patient pressure signal;
    determining a second amplitude of an oscillatory component of a gas flow provided to the patient at the end of the expiratory phase based on the patient flow signal;
    determining a first resistance value based on a ratio of the first amplitude to the second amplitude, wherein the first resistance value is an equivalent resistance value that represents a parallel combination of an upper airway resistance of the patient and a leak orifice resistance attributable to the patient circuit at the end of the expiratory phase;
    determining an upper airway resistance value based on the first resistance value; and
    using the upper airway resistance value to adjust a therapy pressure delivered to the patient by the gas delivery system as an airway patency of the patient changes during sleep.

2. The method according to claim 1, wherein the determining an upper airway resistance value based on the first resistance value comprises determining the leak orifice resistance and determining the upper airway resistance value using the first resistance value and the leak orifice resistance.

3. The method according to claim 2, wherein the determining the upper airway resistance value using the first resistance value and the leak orifice resistance is based on $$R_{lung} = \frac{R_{equiv} \cdot R_{leak}}{R_{leak} - R_{equiv}},$$

where $R_{lung}$ is the upper airway resistance value, $R_{equiv}$ is first resistance value and $R_{leak}$ is leak orifice resistance.

4. The method according to claim 1, wherein a leak from the patient circuit is ignored and the upper airway resistance value is determined to be the first resistance value.

5. The method according to claim 1, wherein the oscillatory pressure is an infrasonic wave.

6. A method of treating estimating an upper airway resistance of a patient using a gas delivery system, comprising:
    generating a flow of breathing gas using a pressure or flow generator of the gas delivery system;
    delivering the flow of breathing gas to the patient through a patient circuit of the gas delivery system;
    superimposing an oscillatory pressure on the flow of breathing gas delivered through the patient circuit using the pressure or flow generator during an expiratory phase of the patient;
    generating a patient pressure signal using a pressure sensor of the gas delivery system during the expiratory phase, the patient pressure signal being indicative of a pressure provided to the patient through the patient circuit,
    generating a patient flow signal using a flow sensor of the gas delivery system during the expiratory phase, the patient flow signal being indicative of a rate of gas flow provided to the patient through the patient circuit;
    determining a first amplitude of an oscillatory component of a gas pressure provided to the patient at an end of the expiratory phase based on the patient pressure signal, including performing a first root mean square calculation on data from the patient pressure signal corresponding to the end of the expiratory phase to calculate the first amplitude;
    determining a second amplitude of an oscillatory component of a gas flow provided to the patient at the end of the expiratory phase based on the patient flow signal, including performing a second root mean square calculation on data from the patient flow signal corresponding to the end of the expiratory phase to calculate the second amplitude;
    determining a first resistance value based on a ratio of the first amplitude to the second amplitude;

determining an upper airway resistance value based on the first resistance value;

using the upper airway resistance value to adjust a therapy pressure delivered to the patient by the gas delivery system as an airway patency of the patient changes during sleep.

7. The method according to claim 6, wherein in the first root mean square calculation patient data from only a single cycle of the oscillatory pressure is used and wherein in the second root mean square calculation data from only the single cycle of the oscillatory pressure is used.

8. The method according to claim 6, wherein the patient pressure signal is generated by the pressure sensor at an outlet of a pressure generating portion of the gas delivery system to which the patient circuit is coupled.

9. The method according to claim 6, wherein the determining the first amplitude includes filtering the patient pressure signal, and wherein the determining the second amplitude includes filtering the patient flow signal.

10. A gas delivery system, comprising:
a pressure or flow generating system adapted to produce a flow of breathing gas;
a patient circuit operatively coupled to the pressure or flow generating system and structured to deliver the flow of breathing gas to the patient;
a pressure sensor;
a flow sensor; and
a controller operatively coupled to the pressure or flow generating system, the controller being structured and programmed to:
cause the pressure or flow generating system to generate the flow of breathing gas and superimpose an oscillatory pressure on the flow of breathing gas during an expiratory phase of the patient;
receive a patient pressure signal generated by the pressure sensor during the expiratory phase, the patient pressure signal being indicative of a pressure provided to the patient through the patient circuit;
receive a patient flow signal generated by the flow sensor during the expiratory phase, the patient flow signal being indicative of a rate of gas flow provided to the patient through the patient circuit;
determine a first amplitude of an oscillatory component of a gas pressure provided to the patient at an end of the expiratory phase based on the patient pressure signal;
determine a second amplitude of an oscillatory component of a gas flow provided to the patient at the end of the expiratory phase based on the patient flow signal;
determine a first resistance value based on a ratio of the first amplitude to the second amplitude, wherein the first resistance value is an equivalent resistance value that represents a parallel combination of an upper airway resistance of the patient and a leak orifice resistance attributable to the patient circuit at the end of the expiratory phase;
determine an upper airway resistance value based on the first resistance value; and
use the upper airway resistance value to adjust a therapy pressure delivered to the patient by the gas delivery system as an airway patency of the patient chances during sleep.

11. The gas delivery system according to claim 10, wherein the determining an upper airway resistance value based on the first resistance value comprises determining the leak orifice resistance and determining the upper airway resistance value using the first resistance value and the leak orifice resistance.

12. The gas delivery system according to claim 11, wherein the determining the upper airway resistance value using the first resistance value and the leak orifice resistance is based on $$R_{lung} = \frac{R_{equiv} \cdot R_{leak}}{R_{leak} - R_{equiv}},$$

where $R_{lung}$ is the upper airway resistance value, $R_{equiv}$ is first resistance value and $R_{leak}$ is leak orifice resistance.

13. The gas delivery system according to claim 10, wherein a leak from the patient circuit is ignored and the upper airway resistance value is determined to be the first resistance value.

14. The gas delivery system according to claim 10, wherein the oscillatory pressure is an infrasonic wave.

15. The gas delivery system according to claim 10, wherein the gas delivery system is a positive pressure support system.

16. A gas delivery system, comprising:
a pressure or flow generating system adapted to produce a flow of breathing gas;
a patient circuit operatively coupled to the pressure or flow generating system and structured to deliver the flow of breathing gas to the patient;
a pressure sensor;
a flow sensor; and
a controller operatively coupled to the pressure or flow generating system, the controller being structured and programmed to:
cause the pressure or flow generating system to generate the flow of breathing gas and superimpose an oscillatory pressure on the flow of breathing gas during an expiratory phase of the patient;
receive a patient pressure signal generated by the pressure sensor during the expiratory phase, the patient pressure signal being indicative of a pressure provided to the patient through the patient circuit;
receive a patient flow signal generated by the flow sensor during the expiratory phase, the patient flow signal being indicative of a rate of gas flow provided to the patient through the patient circuit;
determine a first amplitude of an oscillatory component of a gas pressure provided to the patient at an end of the expiratory phase based on the patient pressure signal, including performing a first root mean square calculation on data from the patient pressure signal corresponding to the end of the expiratory phase to calculate the first amplitude;
determine a second amplitude of an oscillatory component of a gas flow provided to the patient at the end of the expiratory phase based on the patient flow signal, including performing a second root mean square calculation on data from the patient flow signal corresponding to the end of the expiratory phase to calculate the second amplitude;
determine a first resistance value based on a ratio of the first amplitude to the second amplitude;
determine an upper airway resistance value based on the first resistance value; and
use the upper airway resistance value to adjust a therapy pressure delivered to the patient by the gas delivery system as an airway patency of the patient changes during sleep.

17. The gas delivery system according to claim 16, wherein in the first root mean square calculation data from only a single cycle of the oscillatory pressure is used and wherein in the second root mean square calculation data from only the single cycle of the oscillatory pressure is used.

18. The gas delivery system according to claim 16, wherein the patient pressure signal is generated by the pressure sensor at an outlet of the pressure or flow generating system.

* * * * *